US006507755B1

(12) United States Patent
Gozani et al.

(10) Patent No.: US 6,507,755 B1
(45) Date of Patent: Jan. 14, 2003

(54) APPARATUS AND METHOD FOR STIMULATING HUMAN TISSUE

(75) Inventors: Shai N. Gozani, Brookline, MA (US); Christopher T. Turner, Somerville, MA (US); Salim Kassem, Malden, MA (US)

(73) Assignee: NeuroMetrix, Inc., Waltham, MA (US)

( * ) Notice: Subject to any disclaimer, the term of this patent is extended or adjusted under 35 U.S.C. 154(b) by 0 days.

(21) Appl. No.: 09/261,402

(22) Filed: Mar. 3, 1999

Related U.S. Application Data

(63) Continuation-in-part of application No. 09/204,032, filed on Dec. 1, 1998.

(51) Int. Cl.$^7$ .................................................. A61B 5/05
(52) U.S. Cl. ........................................ 600/547; 607/57
(58) Field of Search ................................ 600/546, 547, 600/587, 585; 607/57, 59, 62

(56) References Cited

U.S. PATENT DOCUMENTS

| | | | | |
|---|---|---|---|---|
| 3,886,931 A | | 6/1975 | Rodler ........................ | 128/2.1 |
| 4,807,643 A | | 2/1989 | Rosier ........................ | 128/741 |
| 5,041,974 A | * | 8/1991 | Walker et al. .......... | 364/413.27 |
| 5,080,099 A | | 1/1992 | Way et al. ................... | 128/640 |
| 5,092,344 A | | 3/1992 | Lee ............................. | 128/741 |
| 5,131,401 A | | 7/1992 | Westenskow et al. ....... | 128/741 |
| 5,143,081 A | | 9/1992 | Young et al. ................ | 128/741 |
| 5,215,100 A | | 6/1993 | Spitz et al. .................. | 128/741 |
| 5,284,154 A | | 2/1994 | Raymond et al. ........... | 128/741 |
| 5,329,902 A | | 7/1994 | Lemmen ..................... | 128/734 |
| 5,333,618 A | | 8/1994 | Lekhtman et al. .......... | 128/734 |
| 5,514,175 A | * | 5/1996 | Kim et al. ................... | 607/136 |

FOREIGN PATENT DOCUMENTS

| | | |
|---|---|---|
| EP | 0 025 222 | 3/1981 |
| WO | 91/16001 | 10/1991 |

OTHER PUBLICATIONS

Basmajian, M.D. et al. (1985), "Apparatus, Detection, and Recording Techniques", *Muscles Alive: Their Functions Revealed by Electromyography*, 5th Ed., William & Wilkin, Baltimore, pp. 19–64.
Carpay et al. (1997), "Coactivation of the ulnar nerve in motor tests for carpal tunnel syndrome", *Neurophysiol Clin.*, 27:309–313.
Chaudhry, M.D. (1997), "Technology Review: Nervepace Digital Electroneurometer", *AAEM Practice Topics in Electrodiagnostic Medicine*, 20:1200–1203.
Hodes (1965), "Low Threshold Associated With Slow Conduction Velocity", *Arch Neurol.*, 12:510–526.
Kimura M.D. (1984), "Principles and Pitfalls of Nerve Conduction Studies", *Ann. Neurol.*, 16:415–429.
Oh, M.D. (1993), "Basic Components of Electromyography Instruments", *Clinical Electromyography: Never Conduction Studies*, 2nd Ed., pp. 26–59.
Preston. M.D. (1994), "Submaximal Stimuli Activate Different Nerve Fiber Populations at Different Sites", *Muscle & Nerve*, 17:381–385.
Shefner, M.D. (1990), "The Use of Sensory Action potentials in the Diagnosis of Peripheral Nerve Disease", *Arch Neurol.*, 47:341–348.

\* cited by examiner

*Primary Examiner*—Kevin Shaver
*Assistant Examiner*—Pamela L Wingood
(74) *Attorney, Agent, or Firm*—Pandiscio & Pandiscio, P.C.

(57) ABSTRACT

A system and method for stimulating human tissue using a master controller and a slave controller that communicate using high level commands. In one embodiment, a system of the invention includes a master controller, a slave controller in signal communication with and electrically isolated from the master controller, and a stimulation circuit in electrical communication with the slave controller and having a stimulation output capable of providing an electrical stimulation to the human tissue. The master controller communicates at least one command comprising at least one parameter to the slave controller, and the slave controller controls said stimulation circuit to stimulate human tissue in response to the command comprising at least one parameter.

27 Claims, 7 Drawing Sheets

APPARATUS AND METHOD FOR STIMULATING HUMAN TISSUE

CROSS-REFERENCE TO RELATED CASES

This application is a continuation-in-part of U.S. patent application Ser. No. 09/204,032, filed Dec. 1, 1998, the contents of which are incorporated by reference.

FIELD OF THE INVENTION

The invention relates to apparatus and methods for providing non-invasive stimulation of human tissue. More specifically, the invention relates to apparatus and methods for non-invasive stimulation to assist in assessing neuromuscular function.

BACKGROUND INFORMATION

There are many clinical and non-clinical situations that call for a rapid, reliable and low-cost assessment of neuromuscular function. The most common causes of neuromuscular disruption are related to pathologies of the peripheral nerves and muscles. Neuromuscular disorders, such as, for example, Carpal Tunnel Syndrome (CTS), are very common and well known to the general public. The disease is thought to arise from compression of the Median nerve as it traverses the wrist. The only objective way to detect CTS is to measure the transmission of neural signals across the wrist.

Formal nerve conduction studies (which can detect and monitor of neuromuscular pathologies such as CTS) are time-consuming, expensive, complicated, and require a trained medical expert. Moreover, these studies are not available in environments where early detection could significantly decrease the rate of CTS, such as the workplace where a significant number of causes of CTS appear. Thus, attempts have been made to make such diagnostic measurements available to non-experts. However, these devices and methods still demand a considerable level of expertise from the operator. For example, prior art devices typically require the operator to manually determine stimulation and detection parameters, such as the magnitude of the electrical stimulus. Prior art devices also typically do not automatically implement the diagnostic procedure and display readily interpretable results.

SUMMARY OF THE INVENTION

The invention relates to a system and method for stimulating human tissue using a master controller and a slave controller that communicate using a command language. In one embodiment of the invention, the system includes a master controller, a slave controller in signal communication with and electrically isolated from the master controller, and a stimulation circuit in electrical communication with the slave controller and having a stimulation output capable of providing an electrical stimulation to the human tissue. The master controller communicates at least one command comprising at least one parameter to the slave controller, and the slave controller controls said stimulation circuit to stimulate human tissue in response to the command comprising at least one parameter.

In one embodiment, the master and slave controllers communicate using a serial line. In another embodiment, the master controller transmits commands to the slave controller over a first communications channel, and the slave controller transmits commands to the master controller over a second communications channel.

In still another embodiment, the slave controller controls the stimulation circuit by converting the at least one command comprising at least one parameter into a sequence of control signals transmitted to the stimulation circuit. In another embodiment, the at least one command comprising at least one parameter comprises a plurality of commands.

In other embodiments of the invention, the system further comprises a sensor having an input terminal in electrical communication to the stimulation circuit and an output terminal in electrical communication to the slave controller, whereby the sensor monitors the stimulation circuit and transmits data related thereto to the slave controller.

In another embodiment, an apparatus of the invention comprises a controller having a plurality of input terminals and at least one output terminal and a stimulation circuit having a plurality of input terminals in electrical communication with the at least one output terminal of the controller, the stimulation circuit also having at least one stimulation output terminal. The stimulation circuit of this embodiment comprises a high voltage generator, a current stimulator, an amplitude control circuit, and a timing control circuit. The controller receives at the at least one input terminal at least one command comprising at least one parameter and transmits a signal to the input terminal of the stimulation circuit to stimulate the human tissue in response to the at least one command comprising at least one parameter.

One embodiment of the high voltage generator has an input terminal that is one of the at least one input terminals of the stimulation circuit and an output terminal. In one embodiment, the high voltage generator creates a high voltage signal accessible to the current stimulator in response to the signal transmitted to the input terminal of said stimulation circuit.

One embodiment of the current stimulator has a plurality of input terminals, and at least one of the plurality of input terminals is in electrical communication with the output of the high voltage generator. The current stimulator also has an output terminal capable of providing a current waveform to human tissue. In one embodiment, the current stimulator generates a current waveform in response to a signal transmitted to the input terminal of the stimulation circuit.

In another aspect, the invention comprises a method for delivering a stimulation signal to human tissue. This method includes the steps of receiving by a slave controller at least one command from a master controller that is electrically isolated from the slave controller, the command comprising at least one parameter, and stimulating the human tissue in response to the control signal. Other embodiments include the steps of converting the at least one command comprising at least one parameter into a sequence of control signals in response to the at least one command, and stimulating the human tissue in response to this sequence of control signals.

DESCRIPTION OF THE DRAWINGS

In the drawings, like reference characters generally refer to the same parts throughout the different views. Also, the drawings are not necessarily to scale, emphasis instead generally being placed upon illustrating the principles of the invention. These and other features of the invention are more fully described below in the detailed description and accompanying drawings, in which.

DETAILED DESCRIPTION OF THE INVENTION

Figure 1:
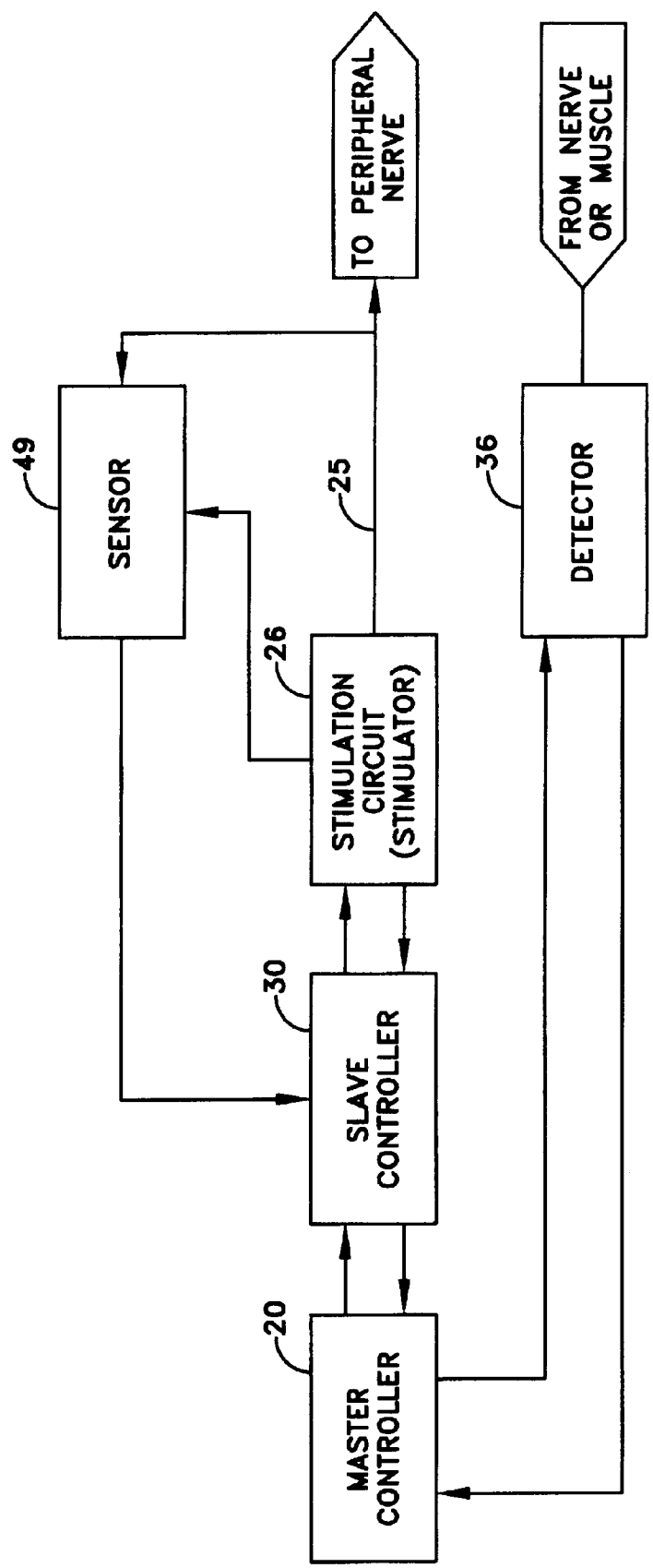
FIG. 1 is a block diagram of an overview of embodiment of a system constructed in accordance with the invention.

FIG. 1 is an overview block diagram of a system constructed in accordance with the invention. A master controller 20 (also called a main controller) is in electrical communication with a slave controller 30 (also called a stimulator controller). The master controller 20 and slave controller 30 are electrically isolated from each other. In one embodiment, an opto-isolator (not shown) isolates each connection between the master controller 20 and the slave controller 30.

A stimulation circuit 26 (also called a stimulator) is in electrical communication with slave controller 30, and has a stimulation output 25 that is capable of providing stimulation to human tissue. After the stimulation has been applied to the human tissue, detector 36 detects biopotentials generated by a nerve or muscle in response to the stimulation for processing the biopotentials and transmits them to the master controller 20. The master controller 20 then processes the received biopotentials.

Figure 3:
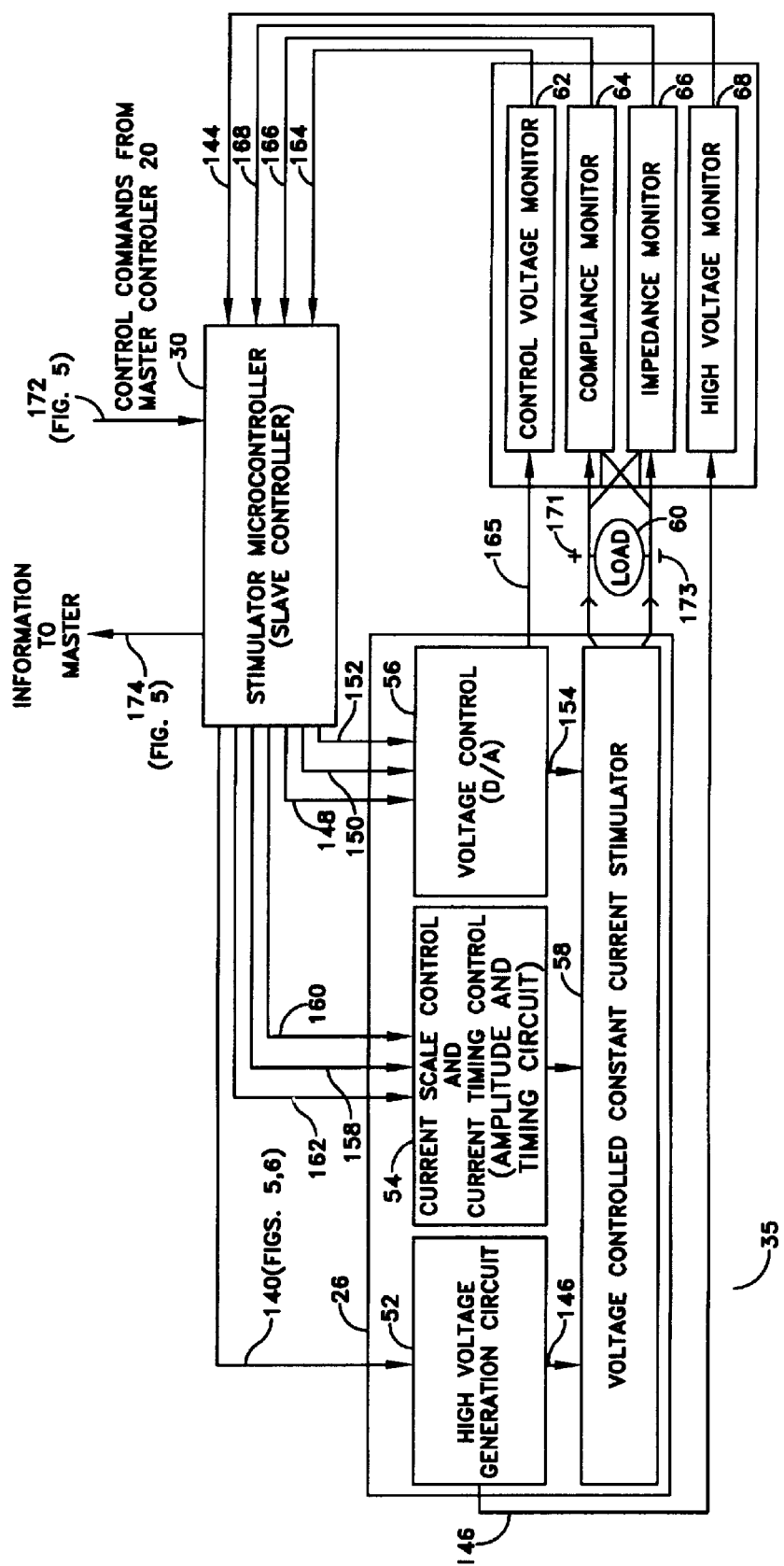
FIG. 3 is a more detailed block diagram of the slave circuit of the embodiment shown in FIG. 2.

Slave controller 30, stimulation circuit 26, and sensor 49 together form a slave circuit 35, which is described in more detail in FIG. 3.

During operation, master controller 20 transmits an instruction to the slave controller 30 using a command comprising at least one parameter. In one embodiment, the command comprises a command language. The parameter of the command is used to provide parameters to the slave controller 30 in order to direct the stimulator 26 to perform specific actions, such as setting a particular stimulus to be applied to the human tissue. For example, in one embodiment of the invention, the master controller 20 sends a command to the slave controller 30 such as STIM 100. The slave controller interprets this as "Stimulate for 100 milliseconds." In another example, the command specifies more than one parameter, such as STIM200X20. This command instructs the slave controller 20 to "Stimulate for 200 microseconds at 20 milliamperes."

Of course, these commands are provided by way of example only. Those skilled in the art will recognize that many commands are usable within the spirit and scope of the invention. Further, the command need not be in the format illustrated above. For example, the command can comprise an eight bit serial command, a series of ASCII characters, a series of ones and zeros, and the like. Any type of command that the slave controller 30 can understand can be used. The command from the master controller 20 is capable of including at least one parameter that the slave controller 30 can interpret to control the stimulation circuit 26 such that it stimulates the human tissue in accordance with the parameter or parameters.

In another embodiment, the eight bit serial commands that are used include functions such as:

1) Turn high voltage generation on
2) Turn high voltage generation off
3) Report measured value of high voltage
4) Set stimulus (amplitude (pulse))
5) Set stimulus (duration (pulse))
6) Stimulate with previously set parameters (pulse)
7) Report amount of current delivered during last stimulus
8) Report measured impedance of load The command examples listed above are provided by way of example only, and it should be understood that many other types of commands can be implemented by those skilled in the art.

After receiving a command, the slave controller 30 parses it, and in turn activates the proper control signals, which it transmits to the stimulation circuit 26, such that the requested action is performed. Operation of the stimulation circuit 26 will be described in greater detail below. After the action (e.g., the stimulation) has been performed, if required, the stimulation circuit 26 transmits information relating to the stimulation, such as a status report concerning the action, back to the master controller 20 via the slave controller 30.

The system further comprises a sensor 49, which has input terminals in electrical communication with the stimulation circuit 26 and an output terminal in electrical communication with the slave controller 30. In one embodiment, the sensor 49 monitors the stimulation signal being transmitted to the human tissue (illustrated by way of example only to be a peripheral nerve) and transmits data related thereto to the slave controller 30. For example, in one embodiment, the sensor 49 monitors the actual current delivered to the load (e.g., tissue) and reports this information to the slave controller 30. In still another embodiment, the sensor 49 monitors the impedance of the human tissue (or other load to which the stimulation is being applied) and reports this information to the slave controller 30. In yet another embodiment, the sensor 49 monitors one or more signals created in the stimulation circuit 26. For example, the sensor 49 may monitor and report the status of a high voltage signal generated in the stimulation circuit 26 that is used to supply a current waveform applied to human tissue. This feature is explained more fully below.

As seen in the above description, the slave controller 30 serves as an interface between the master controller 20 and the stimulation circuit 26. Thus, the implementation of the invention using a simple interface with a command language means that complexity and new features can be added to the stimulator circuit 26 without significantly increasing the complexity of the master controller 20. Thus, because the slave controller 30 can parse commands received from the master 20 into control signals usable by whatever stimulation circuit 26 is in electrical communication with the slave controller 30, software running on the master controller 20 does not necessarily have to change whenever the stimulation circuit 26 changes.

Figure 2:
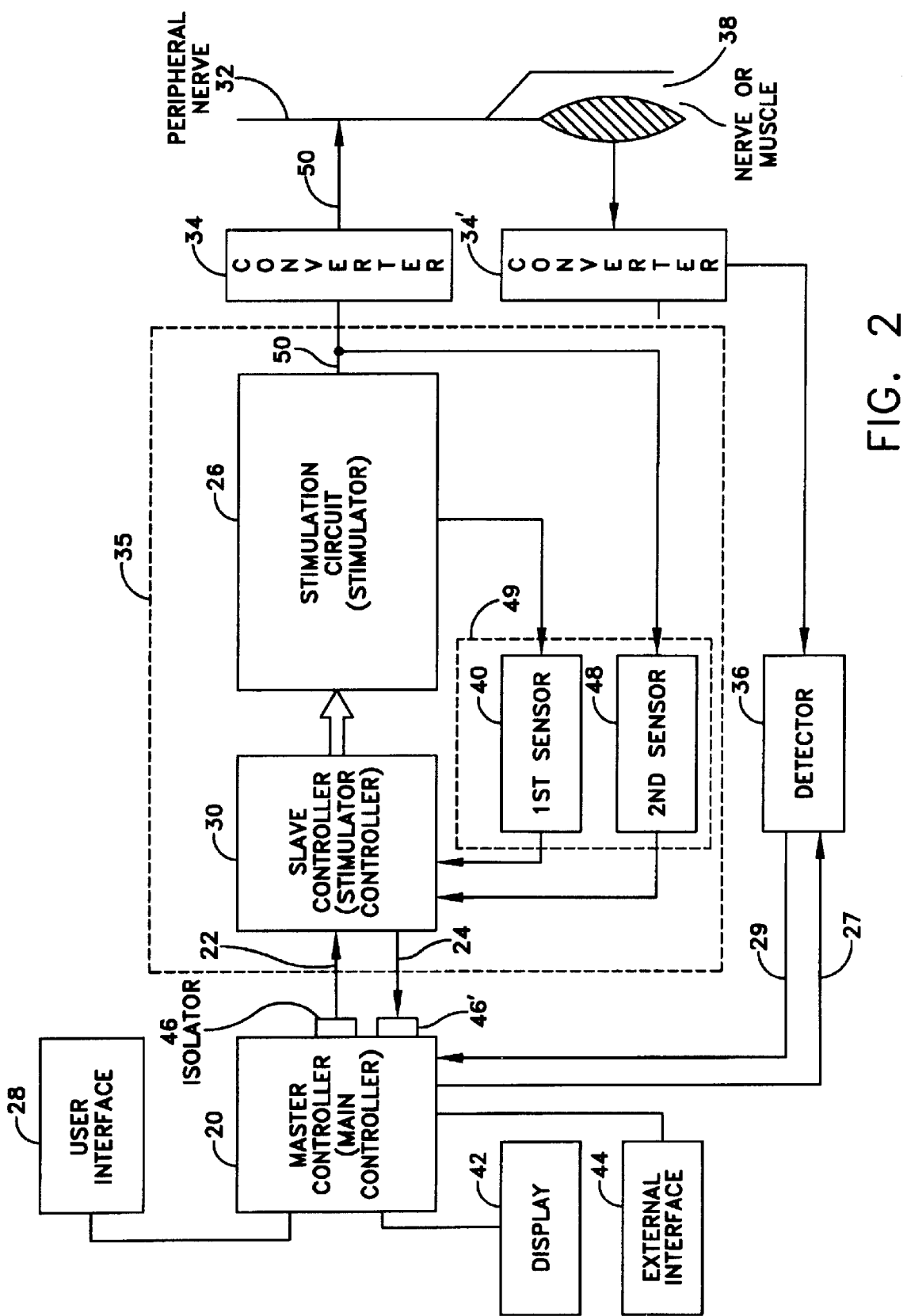
FIG. 2 is a more detailed block diagram of the embodiment of the system shown in FIG. 1.

A more detailed block diagram of the embodiment of the system of FIG. 1 is shown in FIG. 2. A main controller 20 transmits commands over a first communications channel 22 to the stimulator controller 30 and receives information from the stimulator controller 30 over a second communications channel 24. As recited above, each command comprises at least one parameter. On each of the first and second communications channels 22, 24, main controller 20 is in electrical communication with stimulator controller 30 through an isolator 46. In a preferred embodiment, isolator 46 is an optical isolator. In addition, main controller 20 communicates with stimulator controller 30 in a master/slave relationship.

Main controller 20 preferably is embodied as a single, integrated, low-cost embedded microcontroller. In other embodiments, main controller 20 has multiple components, such as, for example, a microprocessor and external components that perform analog-to-digital conversion and other necessary functions.

In response to commands sent from the main controller 20 to the stimulator controller 30, the stimulator controller 30 performs one or more actions. In one embodiment, the stimulator controller 30 generates one or more control signals for generating a stimulus, in response to the command. The one or more control signals are transmitted to the stimulation circuit 26. One or more parameters of the stimulus or stimuli are determined by the control signals from stimulator controller 30 (which receives its commands from the master controller 20). Thus, the stimulator 26 generates a stimulus in response to a command having a parameter that is sent from the main controller 20 to the stimulator controller 30. In another embodiment, in response to a command from the main controller 20, the stimulator controller 30 transmits information to the master controller 20, such as information relating to signals generated in and/or by the stimulator 26.

In a preferred embodiment, stimulator controller 30 is a single, integrated, low-cost embedded microcontroller. In a preferred embodiment, the stimulus or stimuli are electrical stimuli of constant current pulses with amplitude and duration controlled by digital signals from stimulator controller 30. Other embodiments include electrical stimuli of constant voltage pulses or arbitrary waveforms. Stimulator 26 delivers stimuli 50 to a peripheral nerve 32 through converter 34 described below. In addition, a first sensor 40 monitors signals generated in the stimulator 26 that are used to form the stimulus 50 and transmits information about these signals to the stimulation controller 30, which transmits the information to the main controller 20 over the second communications channel 24. The monitoring functions of first sensor 40 are described in further detail below.

Converter 34 includes a bioelectrical interface or any other means to convert electronic signals into bioelectrical signals that pass through the skin surface. In a preferred embodiment, converter 34 is a conventional silver/silver-chloride biomedical electrode located on the skin surface and is in electrical communication with stimulator 26.

Detector 36 detects biopotentials generated by a nerve or muscle 38. In a preferred embodiment, detector 36 is a high input impedance, high common mode rejection instrumentation amplifier followed by signal conditioning circuitry that amplifies and filters biopotentials prior to digitization of the signals by main controller 40. Detector 36 also performs variable gain amplification of the detected biopotentials. Gain control for the detector 36 is established by digital signals 27 from the main controller 20. Detector 36 detects the biopotentials through a converter 34'. Converter 34' converts bioelectrical signals at the skin surface into electronic signals. In a preferred embodiment, converter 34' also is a conventional silver/silver-chloride biomedical electrode located on the skin surface and in electrical communication with detector 36. A second sensor 48 monitors the electrical signals converted by converter 34 and provides information related to these signals to slave stimulation controller 30, which passes them on to the main controller 20 (if required).

The output of detector 36 is in electrical communication 29 with an input of the main controller 20, which then digitizes, processes, and stores the waveforms acquired by the detector 36. In one embodiment, main controller 20 analyzes the waveforms. The parameters extracted from the waveforms include, but are not limited to, the peak amplitude of the waveform, the delay between the onset of the stimulus and the onset of the waveform, and the delay between the onset of the stimulus and the peak of the waveform. In one embodiment, main controller 20 also calculates and processes first and second derivatives of detected waveforms prior to extraction of the above-listed parameters.

In another embodiment of the invention, the apparatus also includes a temperature sensor (not shown) for measuring the temperature of the surface of the skin that is above the nerve or muscle enervated by the nerve from which conduction measurements are being taken. In this embodiment, the temperature sensor is in electrical communication with stimulation controller 30, which transmits the information to main controller 20, which adjusts the parameters described above in response to the skin temperature. In another embodiment, the temperature sensor is in electrical communication with main controller 20 and transmits the information directly to the main controller 20.

In one embodiment, the invention includes a user interface 28, which allows the operator to interact with the apparatus. User interface 28 is in electrical communication with main controller 20. In a preferred embodiment, user interface 28 includes momentary pushbutton switches. Display 42 is also in electrical communication with main controller 20 and provides visual feedback to the operator regarding the results of the nerve conduction measurement or provides messages should measurement errors occur. In a preferred embodiment, display 42 is a liquid crystal display.

In another embodiment, the invention includes an external interface 44 that permits the apparatus to communicate with external devices, such as a personal computer or a modem. The external interface 44 is preferably in electrical communication with main controller 20 and is preferably embodied as an infra-red serial communication link. The external interface 44 is used to couple with external devices for evaluating nerve conduction parameters and for indicating those parameters to a user.

FIG. 3 is a block diagram showing the slave circuit 35 of FIGS. 1 and 2 in more detail. In this embodiment, the invention is implemented such that it receives one or more commands from a master system (such as a master controller), each command comprising at least one parameter, performs various actions based on those commands, and communicates information about the results of those actions to the master. As described herein, a preferred embodiment of the invention, such as illustrated in FIG. 3, is capable of:

1) Generating a high voltage (>200 V);
2) Monitoring and reporting the status of the generated high voltage;
3) Constant current stimulation with digitally controlled amplitude using feedback to ensure accurate amplitude;
4) Constant current stimulation with pulses, sinusoids, or arbitrary waveforms;
5) Monitoring actual current delivered to the load and reporting this information; and
6) Monitoring the impedance of the load and reporting this information.

Slave controller 30 receives at least one command from the master controller 20 (see FIG. 2) at its receive input terminal 172 and transmits information back to master controller 20 from its transmit output terminal 174. Slave controller 30 has a plurality of output terminals 140, 148, 150, 152, 158, 160, 162, and at least a portion of these output terminals 140, 148, 150, 152, 158, 160, 162 are in electrical communication with subsystems of the stimulation circuit 26. Each output terminal 140, 148, 150, 152, 158, 160, 162 transmits one or more control signals to parts of the stimulation circuit 26, to set up one or more stimulus parameters in accordance with the command sent by master controller 20.

In this embodiment, output terminal 140 of slave controller 30 transmits a control signal that enables and disables the high voltage generator circuit 52. Output terminals 148, 150, 152 of slave controller 30 transmit a control signal that sets a control voltage in the voltage control circuit 56 that helps to set a current range for the current stimulator circuit 58. Output terminals 158, 160 of slave controller 30 transmit a control signal to amplitude and timing circuit 54 that sets the duration of the stimulus. In addition, output terminal 162 of the slave controller 30 transmits a control signal to an amplitude and timing circuit 54 that controls the flow of current during and after stimulation, so that both terminals of the load 60 are brought to the same voltage as quickly as possible.

The slave controller 30 of this embodiment also has a plurality of input terminals 144, 164, 166, 168 in addition to the input terminal 172 that receives commands from the master. These signals transmitted to these input terminals are described in greater detail below.

High voltage generation circuit 52 has an input terminal in electrical communication with the output terminal 140 of the slave controller 30 and an output terminal 146 in electrical communication with the current stimulator circuit 58. In this embodiment, the high voltage generation circuit 42 provides a high DC voltage to the output terminal 146, which transmits it to the current stimulator circuit 58. In one embodiment, the level of the high voltage is greater than 200 volts DC.

In addition, in the embodiment illustrated in FIG. 3, the output terminal 146 of the high voltage generation circuit 52 is in electrical communication with high voltage monitor circuit 68. The high voltage monitor circuit 68 monitors the value of the generated high voltage and reports this value to input terminal 144 of slave controller 30. If required, the slave controller 30 can report this information to the master controller 20 (FIG. 1)

To minimize size and power requirements for the system, in one embodiment, the high voltage generation circuit 52 is implemented using an electroluminescent lamp driver integrated circuit (IC) that uses a switched mode IC driver. This embodiment of the high voltage generation circuit 52 is explained in more detail below with reference to FIG. 6.

The voltage controlled constant current stimulator circuit 58 (hereinafter "current stimulator 58") is a voltage controlled feedback circuit. Control signals 148, 150, 152 sent from stimulator microcontroller 30 to voltage control circuit 56 set a digital amplitude value that the voltage control circuit 56 converts to an analog control voltage 154. The control voltage 154 is provided to the current stimulator circuit 58 to set the magnitude of the current to be applied to the load 60. In one embodiment, modulating the value of the digital control signals generates arbitrary current waveforms at the current stimulator circuit 58.

In addition, the control voltage 154 that is transmitted on the output terminal of the voltage control circuit 56 is also transmitted to output terminal 165 of voltage control circuit 56, which is in electrical communication with a control voltage monitor 62. The control voltage monitor 62 monitors the voltage and provides information about the voltage to the input terminal 164 of slave controller 30. This allows slave controller 30 to adjust the control signals 148, 150, 152 until the voltage read at output terminal 165 of the voltage control circuit 56 precisely matches the value necessary to satisfy the command transmitted from master controller 20 (FIG. 1). This type of closed loop error control eliminates errors due to component tolerances and ensures an accurate amplitude for the control voltage 154.

Amplitude and timing control circuit 54 sets precise timing for pulses of current generated by the current stimulator 58. The current stimulator 58 has output terminals 171, 173 for applying the stimulus to the load 60. The load 60 typically will be human tissue. Because the impedance of the load 60 can vary, impedance monitor 66 monitors the value of the voltage across the load for a known current to yield the impedance of the load at the frequency of stimulation. In one embodiment (for purely resistive loads), the slave controller 30 controls the stimulation circuit to provide a DC stimulation, typically a low current level stimulation. In another embodiment, for a load 60 that is both resistive and capacitive (which it more typical), the slave controller 30 controls the stimulation circuit 26 to apply a low frequency sinusoidal stimulation to the load. The impedance monitor then transmits this information to the slave controller 30, which sends it to the master controller 20 if required. The impedance at that particular frequency can then be determined. If desired, the process can be repeated at multiple frequencies.

Compliance monitor 64 helps the slave controller 30 to monitor the actual current delivered to load 60 during stimulation. In one embodiment, the compliance monitor 64 monitors the control voltage delivered to load 60 and transmits it to input terminal 166 of slave controller 30. This control voltage is then compared with the control voltage 165 monitored by control voltage monitor 62. That is, the control voltage provided to the current stimulator 58 (which is available at output terminal 165) is compared to the control voltage measured at the load 60. If the load 60 is stimulated as specified by the control signal that the slave controller 30 sent to the voltage control circuit 58, then the control voltage provided to the current stimulator 58 will be the same as the control voltage measured at the load. If the load 60 was not stimulated as specified, then the control voltage at the load will be different from the control voltage provided to the current stimulator 58.

Additional details of each of these circuits are described below with respect to FIGS. 5, 6, and 7.

Figure 4:
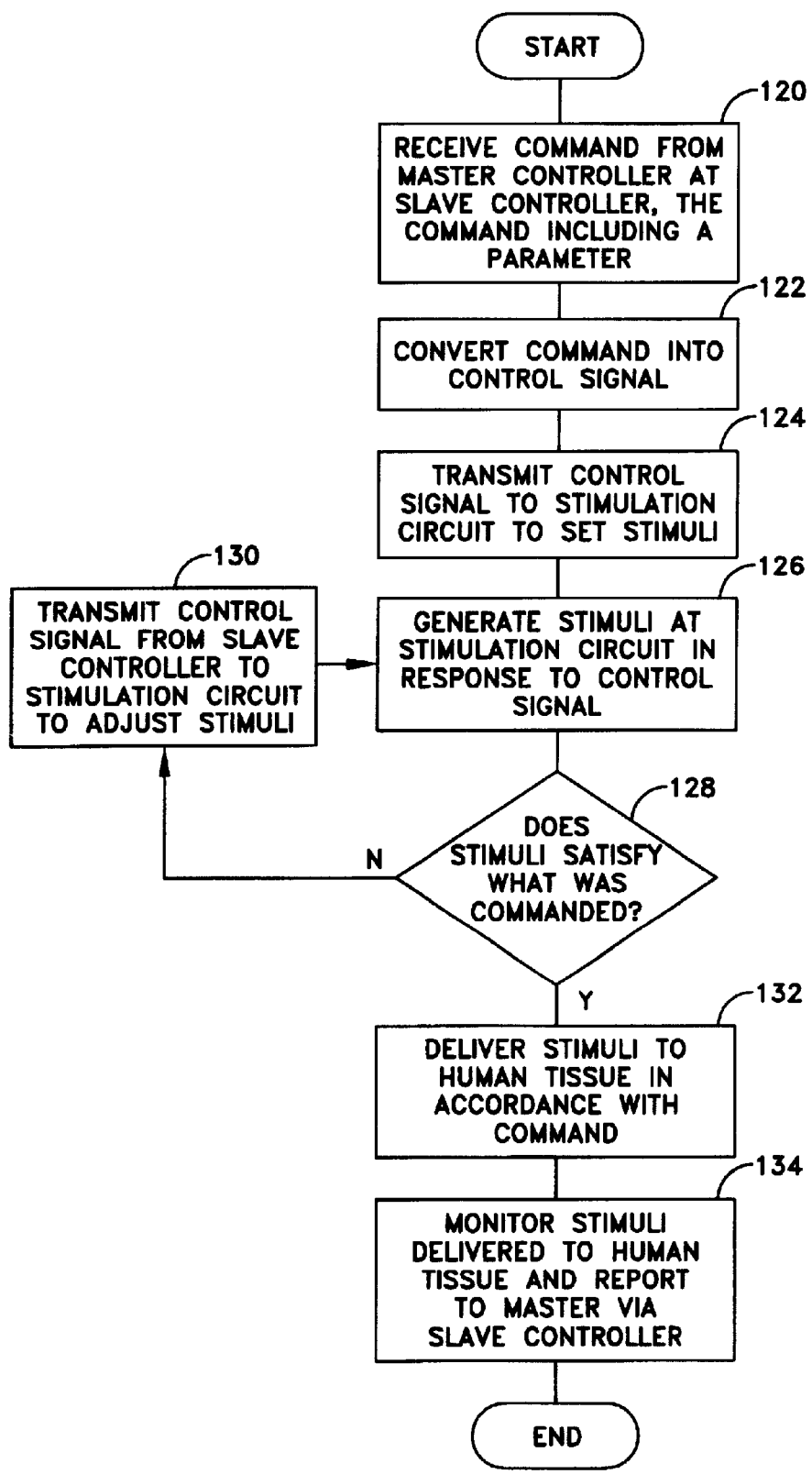
FIG. 4 is a flow chart of an embodiment of a method of producing a stimulation signal.

FIG. 4 is a flow chart of a method for delivering a stimulation signal to human tissue, in accordance with another embodiment of the invention. The slave controller 30 receives a command from the master controller 20, the command including at least one parameter (step 120). The slave controller 30 then parses the command so that the slave controller 30 can convert the command to one or more control signals (step 122). As discussed above, the one or more parameters of the command are used to set variables in the slave controller 30 to direct a stimulator to perform specific actions, such as setting a particular stimulus to be applied to the human tissue. Thus, the slave controller 20 transmits the control signal to a stimulation circuit 26 to set the particular stimulus or stimuli to be applied to the human tissue (step 124).

During generation of the stimulus (step 126), the stimulus is checked to determine if it satisfies the one or more parameters that were part of the command (step 128). For example, in one embodiment, the amplitude level of the stimulus is checked to verify that it satisfies an amplitude parameter specified in step 120 and controlled in step 124. If it does not, then the slave controller 30 transmits one or more additional control signals to the stimulation circuit 26 to adjust the stimulus (step 130). If the stimulus satisfies the value set in the command parameter, then the stimulus is delivered to the human tissue in accordance with the command (step 152). In addition, in this embodiment, the stimulus delivered to the human tissue is also monitored and information relating to the stimulation is reported to the slave controller 30, which reports it to the master controller 20 (step 134).

Figure 5:
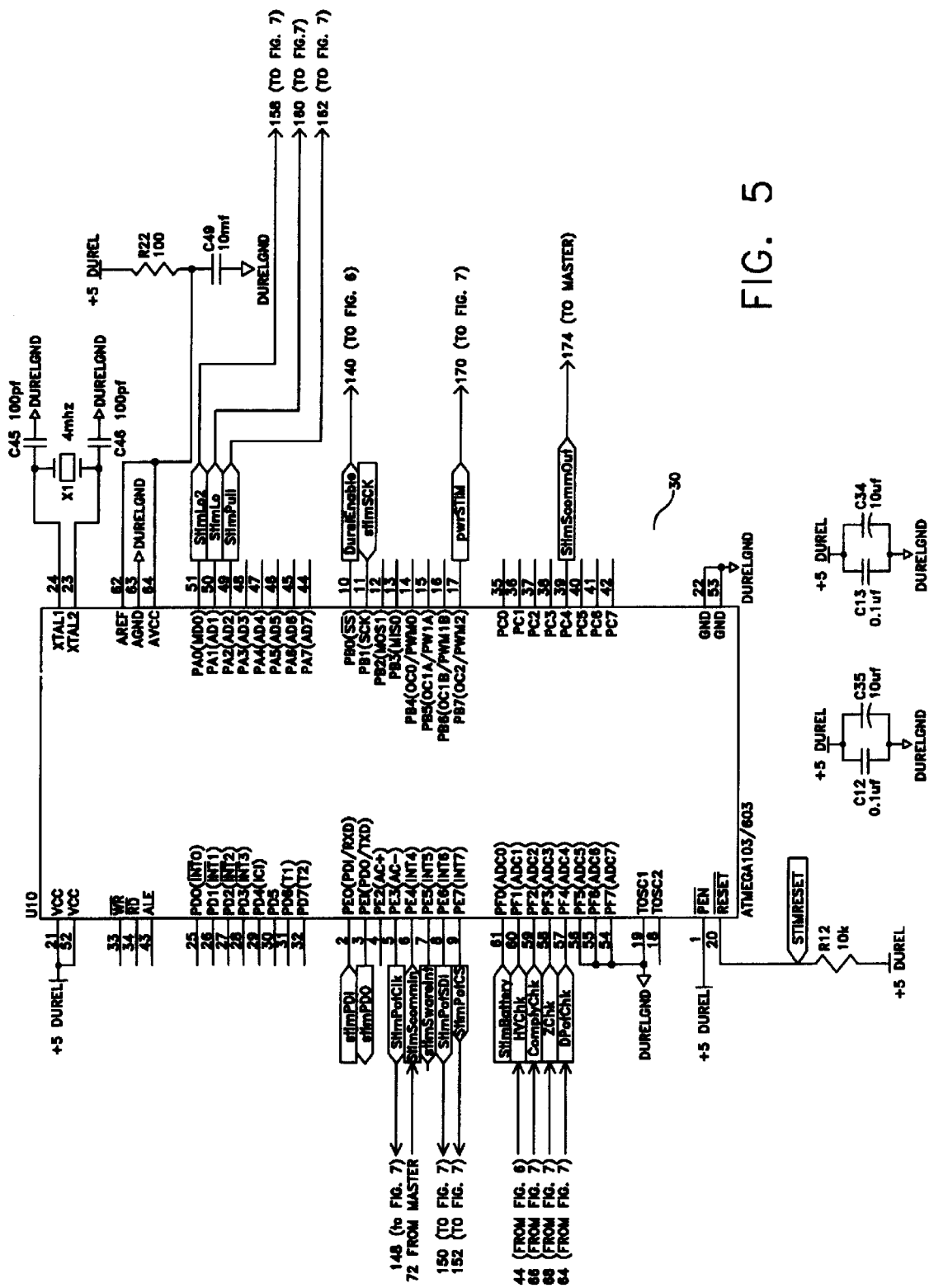
FIG. 5 is a block diagram of an embodiment of the slave controller using the slave circuit shown in FIG. 3.

FIG. 5 illustrates an embodiment of a type of microcontroller that can be used for the stimulator controller 30 of FIGS. 1, 2, and 3, as well as for the master controller 20. Generally, this embodiment of the invention can be controlled by and communicated with over a very simple interface. In the embodiment of FIG. 5, a microcontroller 30 serves as the slave controller 30 of FIGS. 1–3 and as an interface to the master controller 20. Control and communication in this embodiment are performed over a two-wire serial interface: input terminal 172 of slave controller 30 receives commands from the master controller 20 and output terminal 174 of slave controller 30 transmits information to the master controller 20. It should be understood that, although a two-wire serial interface is illustrated in this embodiment, other methods of interface are possible, including single wire interfaces, more than three wires (e.g., ribbon cables), and wireless control.

Referring again to slave controller 30 of FIG. 5, output terminal 140 transmits a control signal to the high voltage generation circuit 52 of FIGS. 1–3 and FIG. 6. Output terminals 142, 148, 150, 152, 158, 160, 162, and 170 of slave controller 30 transmit control signals to the stimulation circuit 26 of FIGS. 1–3 and to the sub-circuits of the stimulation circuit 26 that are illustrated in more detail in FIG. 7. Input terminal 144 of slave controller 30 receives information from the output of the high voltage generation circuit 52 of FIGS. 1–3 and 6. Input terminals 164, 166, and 168 receive information from the stimulation circuit 26 and its subsystems. All of these signals are discussed in more detail below.

In one embodiment of the invention, the stimulator 26 (see FIGS. 1–3 and 7) is specified to deliver stimuli up to 20 milliamperes in magnitude to a 10 kilohm load (typically human tissue). Voltages as great as 200 volts DC are required across the load and must therefore be generated by the stimulator 26. As discussed previously, it is preferred that an apparatus embodying the invention be small and have minimal power requirements. Further, as discussed in connection with FIG. 3, it is preferable to generate the high voltage using an electroluminescent lamp driver integrated circuit (IC) that uses a switched mode IC driver.

Figure 6:
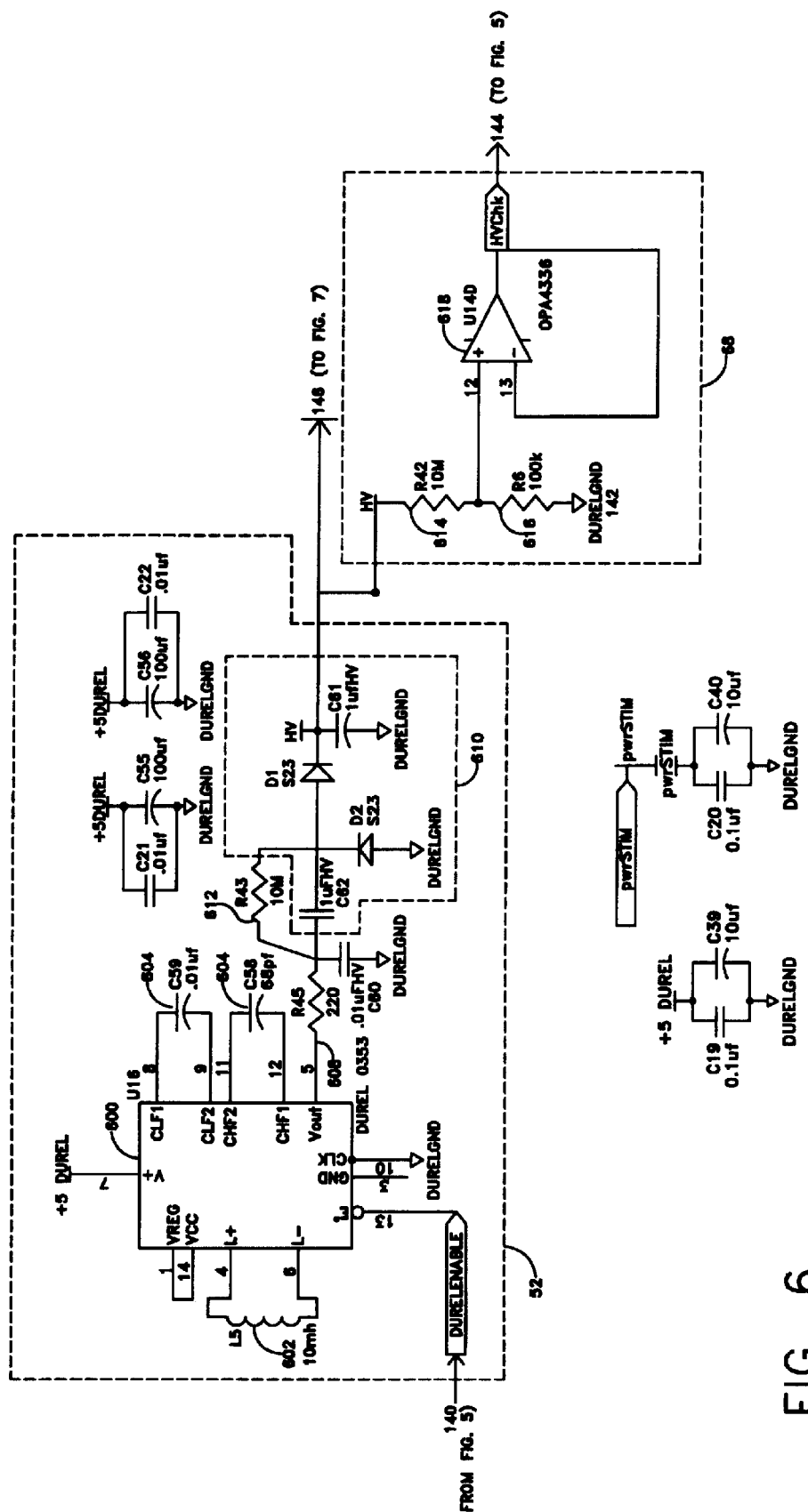
FIG. 6 is a schematic diagram of an embodiment of the high voltage generator used in the slave circuit shown in FIG. 3.

FIG. 6 is a schematic diagram of an embodiment of the high voltage generation circuit, in accordance with such an embodiment of the invention. Referring to FIG. 6, in this embodiment, the high voltage is generated by using an electroluminescent lamp driver integrated circuit 600 (hereinafter "inverter 600") such as the D353 inverter manufactured by Durel Corporation, 2225 W. Chandler Blvd., Chandler, Ariz. 85255-6155. This device is a small integrated circuit that is capable of taking a 5 volt DC voltage at its input and produces an AC output up to 250 Volts peak to peak at its output. As described below, the AC output of inverter 600 is then doubled and rectified to achieve a minimum 200 volt DC output. The DUREL D353 inverter is provided by way of example only; those skilled in the art will appreciate that other types and brands of inverters can be used for the inverter 600. Further, inverter 600 can be replaced by any circuit capable of taking a low DC voltage and producing a high DC output, as understood by those skilled in the art.

As used in this embodiment, inverter 600 requires external inductor 602 and external capacitors 604, 606. In addition, inverter 600 also has an enable input in electrical communication with output terminal 140 of slave controller 30. The inverter is thereby controlled by the slave controller 30 (see FIG. 4). When enabled, the inverter 600 generates an AC high voltage output 608. AC output 608 is then doubled and rectified by a two diode/two capacitor voltage multiplier 610 to produce an output voltage on terminal 146. The output of the multiplier 610 is a minimum 200 volt DC signal that is used as the voltage source for the current stimulator 58 (see FIGS. 1–3 and 7). Resistor 612 drains charge off of one of the capacitors in multiplier 610 when the inverter 600 is disabled so that no residual high voltage will remain. Similarly, resistors 614, 616 drain charge off of the other capacitor of multiplier 610 when the inverter 600 is disabled.

Additionally, the high voltage on terminal 146 is also divided down resistively (resistors 614, 616), buffered by an operational amplifier ("op amp") follower 618 and transmitted to input terminal 146 of slave controller 30 (see FIG. 5). In the embodiment of the slave controller shown in FIG. 5, input terminal 146 is an analog to digital (A/D) converter input of slave controller 30 (i.e., "ADC1"). Providing at least a portion of the high voltage output to the slave controller 30 via high voltage monitor 68, as illustrated in FIGS. 5 and 6, allows the slave controller 30 to monitor the value of the generated high voltage and report this value to the master controller 20 (FIGS. 1 and 2) if required.

As one skilled in the art recognizes, higher voltages can be generated by addition of circuitry to the multiplier circuit 610. This permits stimulation at higher amplitude levels into a given load.

Figure 7:
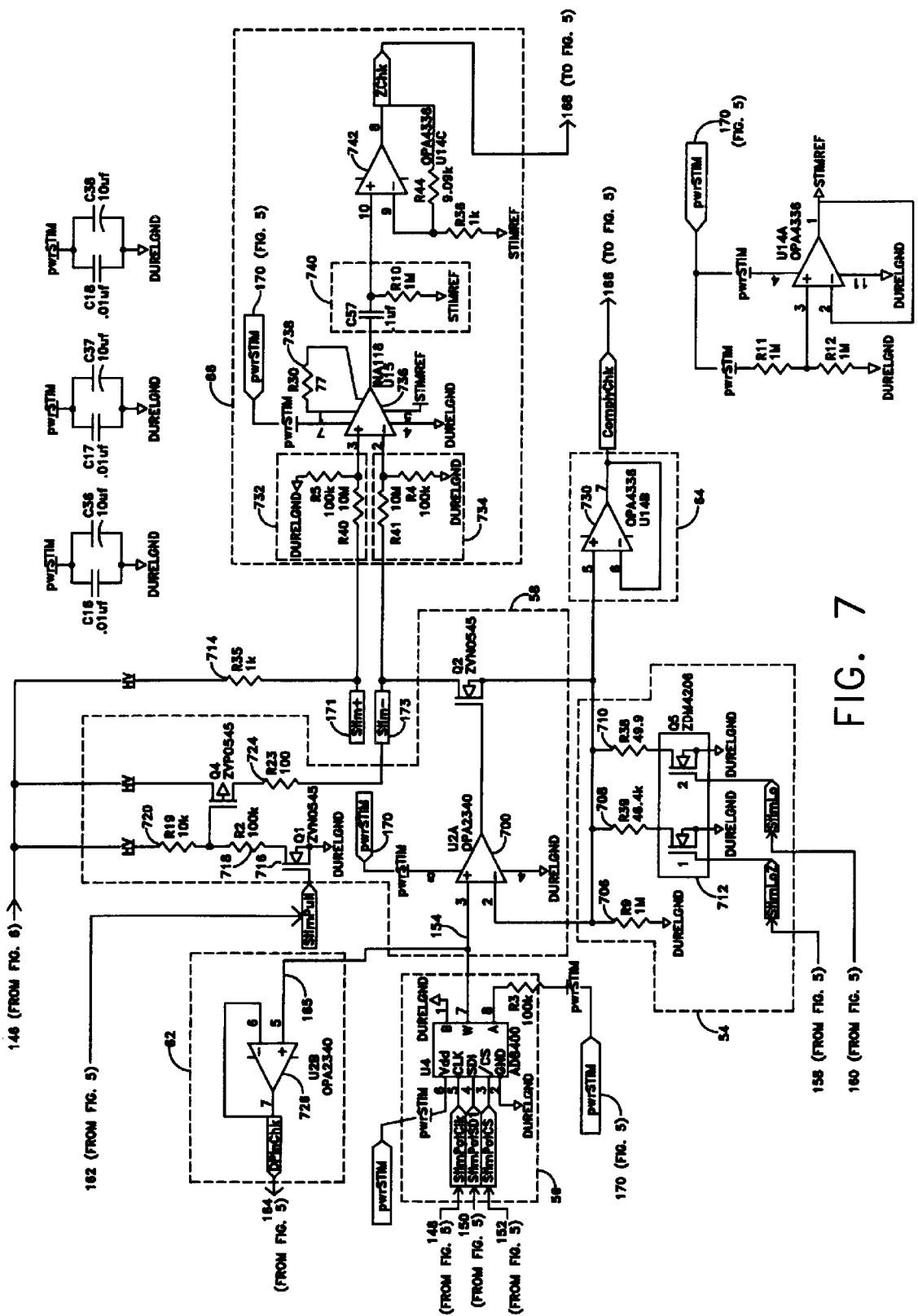
FIG. 7 is a schematic diagram of a portion of an embodiment of the stimulation circuit shown in FIG. 3.

FIG. 7 illustrates part of a stimulation circuit 26 (see FIGS. 1–3) in accordance with one embodiment of the invention. The circuit includes a current stimulator circuit 58, a control voltage monitor circuit 62, an impedance monitor circuit 66, a current timing control circuit 54, and a voltage control circuit 56.

Referring to FIGS. 5 and 7, op amp 700 and field effect transistor 702 form the "heart" of the constant current stimulator. First, slave controller 30 transmits control signals from its output terminals 148, 150, 152 to apply a digital control value to potentiometer 704, which converts the digital control value to an analog control voltage 154. The analog control voltage 154 is applied to the non-inverting input terminal of op amp 700. The inverting terminal of op amp 700 is connected to the source terminal of transistor 702 and the output terminal of op amp 700 is connected to the gate terminal of transistor 702. Because of negative feedback, the op amp 700 will equalize the voltage at its input terminals. Thus, the voltage at the inverting terminal will also be equal to the analog control voltage 154. Therefore, a current proportional to the analog control voltage 154 divided by some parallel combination of the resistors 706, 708, 710 (depending on whether dual transistor 712 is in an "on" state) will flow through transistor 702. To allow this current to flow, a certain voltage must be set up between the gate and source terminals of transistor 702. The output terminal of op amp 700 will assume whatever value is necessary to allow this current to flow.

Because the current flows through transistor 702 it also flows through the load (that is between the stimulation terminals 171 and 173) and resistor 714. The duration of the stimulation is controlled by the dual transistor 712 and will be described in more detail below.

The circuit formed by transistors 716 and 722 and resistors 718, 720, and 724 acts as a "pull-up" circuit for the current stimulator circuit 58. Upon receiving a control signal from output terminal 162 of slave controller 30, this pull-up circuit is disabled so that no current flows through resistor 724 and transistor 722 during stimulation. At the end of the stimulus (for example, at the end of a pulse) transistor 722 is turned on (by transistor 716) and current flows through resistor 724. This ensures that both terminals of the load 171, 173 are brought to the same voltage as quickly as possible.

Amplitude and timing control circuit 58, as described previously, sets the amplitude and timing of the current applied to the load. The amplitude of the current applied to the load is controlled primarily by two factors:

1) The control voltage at the non-inverting terminal of op amp 700, and
2) The magnitude of the resistance between the inverting terminal of op amp 700 and ground.

The amount of current that is applied to the load is calculated using Ohm's law and is the analog control voltage 154 divided by the magnitude of the resistance between the inverting terminal of op amp 700 and ground. For example, if the state of dual transistor 712 is set such that the transistor connected to resistor 708 is off and the transistor connected to resistor 708 is on, then the resistance would be 1 megohm in parallel with 49.9 ohms. This parallel resistance is approximately fifty ohms. Thus if the analog control voltage 154 is set to 1 V, then a current of 1 V/50 ohms, or 20 milliamperes will be applied to the load.

Resistor 706 is provided for stability of the system. The resistors 708 and 710 are provided for setting two different current ranges. For stimulation in the range 1 to 20 milliamperes, the transistor of dual transistor 712 that is connected to resistor 710 is activated. For currents in the range of 1 to 20 microamperes, the transistor that is connected to resistor 708 is activated. Resistor 706 is large enough that its value does not appreciably affect the amount of current flow, regardless of which range is chosen.

The analog control voltage 154 is also transmitted to the op amp follower 726, which transmits it to input terminal 164 of slave controller 30. Thus, slave controller 30 is able to monitor the control voltage that is generated as a result of the control signals sent from output terminals 148, 150, 152 of the slave controller 30 to the voltage control circuit 56. This allows the slave controller 30 to adjust the control signals that it transmits on output terminals 148, 150, 152 until the analog control voltage 154 precisely matches whatever value is desired (i.e., commanded by the master 20 of FIGS. 1 and 2). This type of closed loop control eliminates errors introduced by the component tolerances of potentiometer 704 and ensures that the analog control voltage 154 has an accurate amplitude.

In the amplitude timing and control circuit 54, the transistors of dual transistor 712 typically are turned on for a very brief period of time, resulting in pulse stimulation. However, in one embodiment, one of the transistors can be left on, and sinusoidal or arbitrary waveforms can be generated for the analog control voltage 154 by transmitting an appropriate sequence of control signals from output terminals 148, 150, 152 of the slave controller 30 to the voltage control circuit 56. In this scenario, the stimulation current varies in time as the analog control voltage 154 changes. This allows for sinusoidal or arbitrary waveform stimulation.

As mentioned above, timing control for pulse stimulation is controlled through dual transistor 712. Typically, slave controller 30 transmits control signal from one of its output terminals 158, 160 to the gate terminal of the corresponding transistor of dual transistor 712 (depending on the desired current range, as discussed above). This results in a stimulation pulse applied at stimulation terminals 171, 173 that has similar duration to the pulse that was applied to the gate terminal. Typically, slave controller 30 generates a control signal at one of its output terminals 158, 160 that comprises a 200 microsecond pulse. In addition, the length of the pulse in the slave controller 30's control signal can be specified by the master controller 20 (see FIG. 2). For example, in one embodiment, the master controller 20 transmits a "set duration" command to the slave controller 30, which parses this command to interpret the correct stimulation pulse to apply to the amplitude timing and control circuit 54.

As discussed above, the amount of current that flows during stimulation is the voltage at the inverting terminal of op amp 700 divided by the resistance between that point and ground. If an apparatus embodying the invention is able to properly stimulate a load, the voltage at the inverting terminal of op amp 700 will be equal to the analog control voltage 154 (that is, the voltage at the non-inverting terminal of op amp 700). However, in some cases the two voltages will not be equal. For example, if the load resistance times the current desired requires a voltage that is greater than 200 V, the system will not be able to stimulate as specified. Thus, it is important to monitor the actual current delivered to the load during stimulation.

The slave controller 30 knows the level of the analog control voltage 154 because op amp follower 726 transmits it to input terminal 164 of slave controller 30, an A/D input terminal (described earlier). By buffering the inverting terminal of op amp 700 with op amp 730 (which is part of the compliance monitor circuit 64) and transmitting this signal to input terminal 166 of slave controller 30 (which is another A/D input terminal), the slave controller 30 can determine whether or not stimulation of the load was successful. If stimulation is successful, the signal level at the output terminals of op amp 700 and of op amp 730 should be equal. If stimulation is not successful, then the signal level at the output terminal of op amp 730 will be different from that at the output terminal of op amp 700. By monitoring these values during stimulation, the slave controller 30 can determine whether the load was stimulated as specified by the control signals that it sent to the stimulator circuit 26. That is, the slave controller 30 can determine if the load was stimulated in accordance with the command comprising a parameter that it received from the master controller 20. The slave controller 30 can then report information related to this measurement to the master controller 20.

Using the impedance monitor circuit 66, the slave controller 30 is able to determine a measure of the impedance of the load. The impedance of a load is equal to the voltage across the load divided by the current flowing through it. This measurement is done by the slave controller 30 transmitting control signals to the stimulation circuit 26 causing the stimulation circuit 26 to apply a known, constant current to the load and measuring the resulting voltage that develops across it.

In one embodiment, the slave controller sends control signals to the amplitude and timing control circuit to select the lower (1 to 20 microamps) current range. As discussed previously, DC current can be used, but will only provide an accurate measure of impedance for purely resistive loads. In another embodiment, for the more typical load that is both resistive and capacitive, the slave controller 30 sends control signals to generate a low frequency sinusoidal stimulation. For example, one embodiment uses a 25 Hz, 12.5 microampere peak sinusoidal stimulus. Referring again to FIG. 7, this is accomplished by leaving the transistor of dual transistor 712 that is connected to resistor 708 on and transmitting control signals 148, 150, 152 in a sinusoidal digital pattern to voltage control circuit 56.

When stimulation occurs, a voltage is developed across the load. The magnitude of this voltage depends on the impedance of the load. Because the current is known, the impedance can be determined by measuring the voltage and dividing by the current. This yields the impedance at that particular frequency. If desired, the process can be repeated at multiple frequencies.

The voltage is measured by impedance monitor circuit 66. First, the voltage across the load is divided down by two 100:1 dividers (732, 734). This division is necessary because there is a large common mode voltage (approximately 200V) present on the load that would destroy the amplifier circuits of the impedance monitor circuit 66 if not divided down to a safe level. Instrumentation amplifier 736 then amplifies the differential voltage across the load (post-division by 100). The gain of this amplifier is set by resistor 738. The high pass filter 740 removes any DC offset from the signal. Finally a further amplification is performed by op amp 742. The output of this op amp 742 is transmitted to input terminal 168 of the slave controller, which is yet another A/D input on slave controller 30.

Preferably, the system described above is implemented in a small package that is highly portable and can be powered by a single AAA battery. However, those skilled in the art will recognize that many types of portable power sources, batteries, power packs, and the like, can be used.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. Accordingly, the scope of the invention is limited only by the scope of the appended claims.

What is claimed is:

1. A system for stimulating human tissue, comprising:
   (a) a master controller;
   (b) a slave controller in signal communication with and electrically isolated from said master controller; and
   (c) a stimulation circuit in electrical communication with said slave controller and having a stimulation output capable of providing an electrical stimulation to said human tissue.

2. The system of claim 1 wherein said slave controller is electrically isolated by an opto-isolator from said master controller.

3. The system of claim 1 wherein said slave controller communicates with said master controller by way of a serial line.

4. The system of claim 1 wherein said slave controller controls said stimulation circuit by converting said at least one command comprising a parameter into a sequence of control signals transmitted to said stimulation circuit.

5. The system of claim 1 further comprising a first communications channel and a second communications channel and wherein said master controller transmits at least one command to said slave controller using said first communications channel and said slave controller transmits data to said master controller using said second communications channel.

6. The system of claim 1 where said at least one command comprising at least one parameter comprises a plurality of commands.

7. The system of claim 1 wherein said system further comprises a sensor having an input terminal in electrical communication to said stimulation circuit and an output terminal in electrical communication to said slave controller, whereby said sensor monitors said stimulation circuit and transmits data related thereto to said slave controller.

8. The system of claim 7 wherein said data is related to the impedance presented to said stimulator output.

9. The system of claim 7 wherein said stimulation comprises a current waveform and wherein said data is related to the characteristics of said current waveform.

10. The system of claim 9 wherein said characteristics comprise timing and amplitude parameters of said current waveform.

11. The system of claim 7 wherein said stimulation circuit further comprises a constant current circuit in electrical communication with said stimulation output and a high voltage generation circuit, and wherein said data is related to a voltage generated by said high voltage generation circuit.

12. An apparatus for stimulating human tissue, comprising:
   a) a controller having a plurality of input terminals and at least one output terminal;
   b) a stimulation circuit having a plurality of input terminals in electrical communication with said at least one output terminal of said controller, and having at least one stimulation output terminal, said stimulation circuit comprising:
      (i) a high voltage generator having an input terminal which is one of said plurality of input terminals of said stimulation circuit and having a high voltage output terminal;
      (ii) a current stimulator having a plurality of input terminals, at least one of said plurality of input terminals in communication with said output of said high voltage generator, said current stimulator having an output terminal which is said stimulation circuit output terminal and is capable of providing a current waveform to human tissue;
      (iii) an amplitude control circuit having an input terminal which is one of said plurality of input terminals of said stimulation circuit and an amplitude control output terminal in electrical communication with at least one of said input terminals of said current stimulator;
      (iv) a timing control circuit having an input terminal which is one of said at plurality of input terminals of said stimulation circuit and a timing control output terminal in electrical communication with at least one of said input terminals of said current stimulator;
   whereby said controller receives at said at least one input terminal at least one command comprising at least one parameter and transmits a signal to the input terminal of said stimulation circuit to stimulate said human tissue in response to said at least one command comprising at least one parameter.

13. The apparatus of claim 12 whereby said high voltage generator creates a high voltage signal accessible to said current stimulator in response to the signal transmitted to the input terminal of said stimulation circuit.

14. The apparatus of claim 12 whereby said amplitude control circuit sets the amplitude of a current waveform capable of being applied to human tissue in response to the signal transmitted to the input terminal of said stimulation circuit.

15. The apparatus of claim 12 whereby said timing control circuit sets the timing of said current waveform in response to the signal transmitted to the input terminal of said stimulation circuit.

16. The apparatus of claim 12 whereby said current stimulator generates said current waveform in response to the signal transmitted to the input terminal of said stimulation circuit.

17. The apparatus of claim 12 further comprising a sensor circuit having an input terminal in electrical communication with said stimulation output of said stimulation circuit, and an output terminal in electrical communication with one of said at least one input terminals of said controller;

whereby said sensor monitors said stimulation output and transmits data related thereto to said controller.

18. The apparatus of claim 12 further comprising a sensor circuit having an input terminal in electrical communication with said amplitude control output and an output terminal in electrical communication with one of said plurality of input terminals of said controller;

whereby said sensor monitors the amplitude of the current waveform output and transmits data related thereto to said controller.

19. The apparatus of claim 12 further comprising a sensor circuit having an input terminal in electrical communication with said high voltage output terminal and an output terminal in electrical communication with one of said plurality of one input terminals of said controller;

whereby said sensor monitors the level of the high voltage signal output and transmits data related thereto to said controller.

20. A method for delivering a stimulation signal to human tissue, comprising:

(a) receiving by a slave controller at least one command string from a master controller that is electrically isolated from said slave controller;

(b) generating a control signal by said slave controller in response to said command; and (c) stimulating said human tissue with a stimulator in response to said control signal.

21. The method of claim 20 wherein:

(i) step (b) further comprises converting said at least one command including at least one parameter into a sequence of control signals, in response to said at least one command including at least one parameter; and (ii) step (c) further comprises stimulating said human tissue in response to said sequence of control signals.

22. The method of claim 20 further comprising monitoring the stimulation of said human tissue and adjusting said control signal in response thereto.

23. The method of claim 20 wherein said command string comprises at least one command and at least one parameter.

24. A system for stimulating human tissue, comprising:

(a) a master controller; and, (b) a slave controller in signal communication with and electrically isolated from said master controller, whereby said master controller communicates at least one command string comprising at least a command and at least one parameter to said slave controller.

25. A system for stimulating human tissue, comprising:

(a) a master controller;

(b) a slave controller in signal communication with and electrically isolated from said master controller;

(c) a stimulation circuit in electrical communication with said slave controller and having a stimulation output capable of providing an electrical stimulation to said human tissue; and (d) a sensor having an input terminal in electrical communication to said stimulation circuit and an output terminal in electrical communication to said slave controller, whereby said sensor monitors said stimulation circuit and transmits data related thereto to said slave controller, wherein said data is related to the impedance presented to said stimulator output.

26. A system for stimulating human tissue, comprising:

(a) a master controller;

(b) a slave controller in signal communication with and electrically isolated from said master controller;

(c) a stimulation circuit in electrical communication with said slave controller and having a stimulation output capable of providing an electrical stimulation to said human tissue; and (d) a sensor having an input terminal in electrical communication to said stimulation circuit and an output terminal in electrical communication to said slave controller, whereby said sensor monitors said stimulation circuit and transmits data related thereto to said slave controller, wherein said stimulation circuit further comprises a constant current circuit in electrical communication with said stimulation output and a high voltage generation circuit, and wherein said data is related to a voltage generated by said high voltage generation circuit.

27. A system for stimulating human tissue, comprising:

(a) a master controller;

(b) a slave controller in signal communication with and electrically isolated from said master controller;

(c) a stimulation circuit in electrical communication with said slave controller and having a stimulation output capable of providing an electrical stimulation to said human tissue; and (d) a detector for detecting biopotentials generated by a nerve or muscle in response to the electrical stimulation provided to the human tissue, said detector being in electrical communication with said master controller.

* * * * *